United States Patent [19]
Davidson et al.

[11] Patent Number: 5,574,232
[45] Date of Patent: Nov. 12, 1996

[54] LIQUID SAMPLE FLOW-THROUGH ANALYSIS CELL

[75] Inventors: Robert A. Davidson, Heber; Edward B. Walker, Ogden, both of Utah

[73] Assignees: Robert Davidson, Herber City; Edward Walker, Ogden, both of Utah

[21] Appl. No.: 457,719

[22] Filed: Jun. 1, 1995

[51] Int. Cl.$^6$ .................................................. G01N 1/00
[52] U.S. Cl. ....................................... 73/864.81; 250/343
[58] Field of Search ............................... 73/61.48, 61.59, 73/64.56, 863, 864.81; 378/57, 66, 67, 196; 356/326, 246; 422/82.05, 80, 81; 250/373, 288, 343

[56] References Cited

U.S. PATENT DOCUMENTS 3,021,427  2/1962  Bayly et al. ............................ 250/343

FOREIGN PATENT DOCUMENTS 0232118  1/1986  Germany ................................ 356/246
247612   4/1969  U.S.S.R. ................................. 356/246

*Primary Examiner*—Robert Raevis
*Attorney, Agent, or Firm*—Michael R. Swartz

[57] ABSTRACT

A flow-through sample cell operable in conjunction with a reflectance or fluorescence spectroscopy apparatus to permit real-time analysis of a liquid sample stream is disclosed. The flow-through sample cell includes a housing and a conical-shaped flow control body positioned within the hollow interior of the housing. A liquid sample stream to be analyzed is introduced into the housing along a flow path tangential to the outer surface of the flow control body so as to cause the liquid sample stream to flow through centrifugal action radially along the outer surface of the conical-shaped flow control body and into a viewing area at the bottom of the sample cell. As the liquid sample stream flows through the viewing area, a real-time analysis of the liquid sample stream may be made by an analyzer device positioned outside the sample cell and adjacent to the viewing area.

5 Claims, 1 Drawing Sheet

LIQUID SAMPLE FLOW-THROUGH ANALYSIS CELL

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

1. Field of the Invention

The present invention relates generally to a flow cell used to hold a liquid sample to be analyzed by a reflectance or fluorescence-type analyzer and, more particularly, to such a cell having a flow-through design to permit accurate and precise real-time analysis of a liquid sample stream where continuous low volume flows are required.

2. Description of the Prior Art

Many industrial operations require constant monitoring and analysis to maintain systems control, optimize processes, and monitor generated waste output. With today's demanding standards for quality and statistical process control in the industrial environment, reliable analytical results are critical for success and maintaining profit. As a result, the use of on-line analyses for process control and industrial-stream monitoring has increased rapidly in recent years. On-line analysis of process streams eliminates excess lag time between sampling and circuit adjustments. Critical analytical information is provided in real time, thus helping maintain optimum process conditions and eliminating excess losses. In addition, multi-element on-line analyses provides additional control parameters to maintain process stream purity and minimize hazardous waste production.

The principal challenge for on-line, real-time analysis is to transfer the analytical method and measurement technique from an operator-intensive batch mode to an automated continuous mode. Appropriate methods require that the analyzer not perturb the sample stream, analysis speed be comparable to the process response time, and the analyzer be reliable for harsh industrial environments.

Energy-dispersive x-ray fluorescence (EDXRF) techniques have been successfully used for many years for on-line elemental analysis of solids, slurries, and liquids. There are significant advantages of portable EDXRF instrumentation over currently used large-scale industrial instrumentation. Commercially installed, on-line EDXRF units typically cost between $100,00 and $200,000 depending on the automation level, application, and configuration. In contrast, bench-top EDXRF models cost between $20,000 to $30,000. Besides lower cost, bench-top models provide portability and flexibility for a variety of industrial applications. In contrast, the large-scale industrial systems are usually non-mobile, permanently installed, and primarily dedicated to a specific application. However, a limitation of portable, bench-top units is the explicit design for manual, batch sampling without on-line capability.

Flow-through sampling cells exist for many different analytical applications, including industrial grade EDXRF on-line instrumentation. However, the lack of EDXRF specialized low-volume flow cells for laboratory and small-scale pilot plant situations render bench-top instruments useless for on-line applications. Real-time changes within the process streams require a representative sample be constantly present at the EDXRF instrument's sample window which has a large diameter surface. Industrial grade flow cells for large-scale industrial processes require gallons of sample per minute, an impractical solution for small streams using low-volume flows. Consequently, there is a need for a flow through cell for bench-top EDXRF instruments to replace the individual sample cups and which is designed for low-volume streams and which allows for rapid response to real-time process stream changes.

SUMMARY OF THE INVENTION

The present invention relates to a flow-through sample cell operable in conjunction with a reflectance or fluorescence spectroscopy apparatus designed to satisfy the aforementioned needs. The flow-through sample cell of the present invention has a design which permits the real-time analysis of a liquid sample stream to be conducted, thus eliminating the delays experienced with conventional batch sampling cups presently utilized. In addition, the flow-through sample cell of the present invention is designed to be used in a laboratory setting where low volume liquid sample stream flows are desired.

Accordingly, the present invention is directed to a flow-through sample cell operable in conjunction with a reflectance or fluorescence spectroscopy apparatus to permit real-time analysis of a low volume liquid sample stream. The flow-through sample cell includes: (a) a housing including a cylindrical body having first and second end portions, a first end wall covering the cylindrical body first end portion and a second end wall covering the cylindrical body second end portion, the cylindrical body and first and second end portions arranged to define a housing hollow interior portion; (b) a flow control body positioned within the housing hollow interior portion and having an outer surface of ever-increasing diameter resulting in a corresponding decrease in the available volume within the hollow interior portion as the outer surface extends between a first end portion and a second end portion of the flow control body; (c) means for introducing a liquid sample stream to be analyzed into the housing hollow interior portion and forcing the liquid sample stream to flow by centrifugal action radially over the flow control body outer surface from the first to the second end portion of the flow control body and increase in flow velocity due to the decrease in available volume within the housing hollow interior portion, the radial flow induced by centrifugal action displacing liquid sample volume within the housing hollow interior portion as the liquid sample stream flows therethrough and thereby permitting a real-time analysis of the liquid sample stream to be conducted after the liquid sample stream leaves the flow control body second end portion; and (d) discharge means for removing the liquid sample stream from the housing hollow interior portion after the real-time analysis has been completed.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the course of the following detailed description, reference will be made to the attached drawings in which.

DETAILED DESCRIPTION OF THE INVENTION

In General

Figure 1:
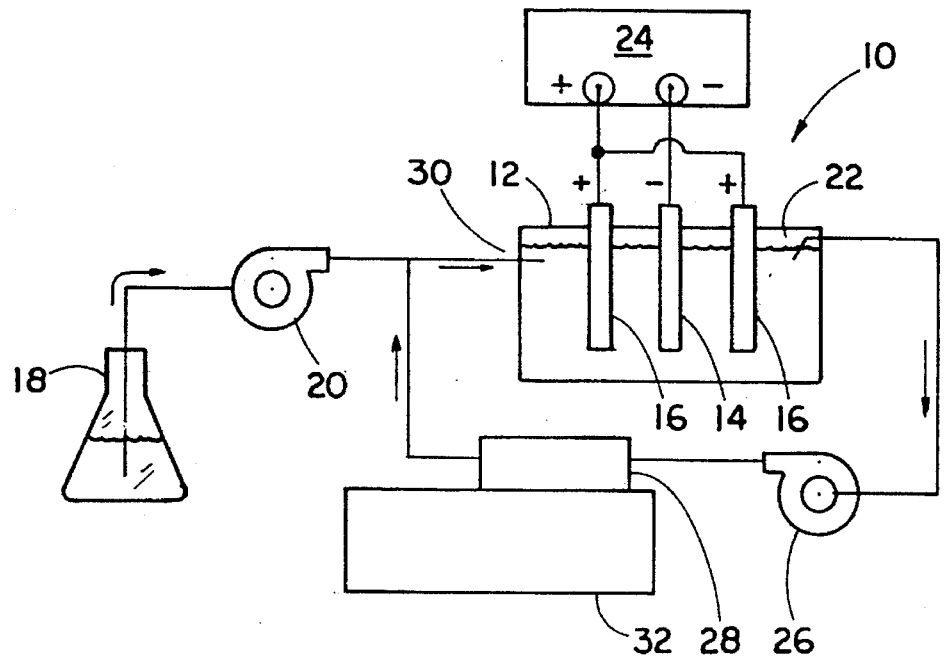
FIG. 1 is a schematic diagram illustrating a copper electrowinning circuit that includes a flow-through sample cell which is the subject of the present invention and is utilized in conjunction with an XRF analyzer to permit the XRF analyzer to perform a real-time analysis of a low-volume liquid sample stream removed from the electrowinning cells of the system.

Referring now to the drawings, and particularly to FIG. 1, there is illustrated a schematic diagram of an electrowinning circuit, generally designated by the numeral 10, which utilizes an electrowinning cell 12 to remove copper from an electrolyte solution. As will be described herein, the flow-through sample cell of the present invention plays an important part in the operation of the electrowinning system 10 due to it's unique construction which permits a real-time analysis of the electrolyte solution removed from the electrowinning cell 12. It should be understood that the flow-through sample cell of the present invention is described in conjunction with the electrowinning circuit 10 for purposes of explanation only and may be used in any other type of electrolyte or liquid system which relies on spectroscopic analyses, such as reflectance or fluorescence-type analysis. In addition, since the electrowinning process is itself well known in the art, only enough explanation of the operation of the electrowinning circuit 10 will be given to appreciate the benefits of the flow-through sample cell of the present invention.

As seen in FIG. 1, the electrowinning circuit 10 includes the electrowinning cell 12 constructed from clear acrylic. A single copper cathode 14, is positioned between two lead anodes 16. A 36.5 g/L copper sulfate electrolyte solution housed in a container 18 is pumped via a controlled feed pump 20 into the interior-of the electrowinning cell 12 and flows across the copper cathode 14 and pair of lead anodes 16 to an overflow drain 22. The electrowinning cell 12 is operated at 9 amps and 2.2 volts delivered from a power supply 24 with a copper cathode surface area of 120 square centimeters. These conditions are capable of removing 1.0687 g of copper per ampere-hour, which gives the electrowinning cell an efficiency of 90%. Analysis of the electrolyte solution is done by pumping a small liquid sample stream removed from the overflow drain 22 via a pump 26 into and through the flow-through sample cell 28 of the present invention and thereafter returning the liquid sample stream to the inlet end 30 of the electrowinning cell 12. As the liquid sample stream flows through the flow-through sample cell 28 of the present invention, an XRF analyzer 32 operates to provide an analysis of the copper entrained in the liquid sample stream.

FLOW-THROUGH SAMPLE CELL OF THE PRESENT INVENTION

As will be described herein, the flow-through sample cell 28 of the present invention has a construction which permits an analyzer such as the XRF analyzer 32 described with respect to FIG. 1 to perform a real-time, on-line analysis of an electrolyte solution flowing through the interior of the sample cell 28. The flow-through sample cell 28 may be used in any laboratory wherever reflectance or fluorescence-type analyses of liquid samples is routinely utilized, e.g., X-ray florescence, colorimetry, or fluorimetry in hospital, medical, environmental, research, metallurgical, geological, biological and chemical laboratories. Any routine batch-type reflectance or fluorescence analysis of liquid samples could benefit using the flow-through sample cell 28 of the present invention for automating instrumental analysis of a low-volume liquid sample stream. These benefits include, among other things, increased liquid sample stream throughput with decreased man hours per analysis and decreased disposable waste normally associated with batch-type analysis. As will be further described herein, the flow-through sample cell 28 of the present invention is capable of permitting a low volume liquid sample stream flowing through it to respond rapidly to changes in a sample stream concentration; within 12 seconds and has a construction which permits the real time analysis of continual flowing liquid sample streams where relatively low sample stream flow rates (i.e.—20 mL/min) are required.

Figure 2:
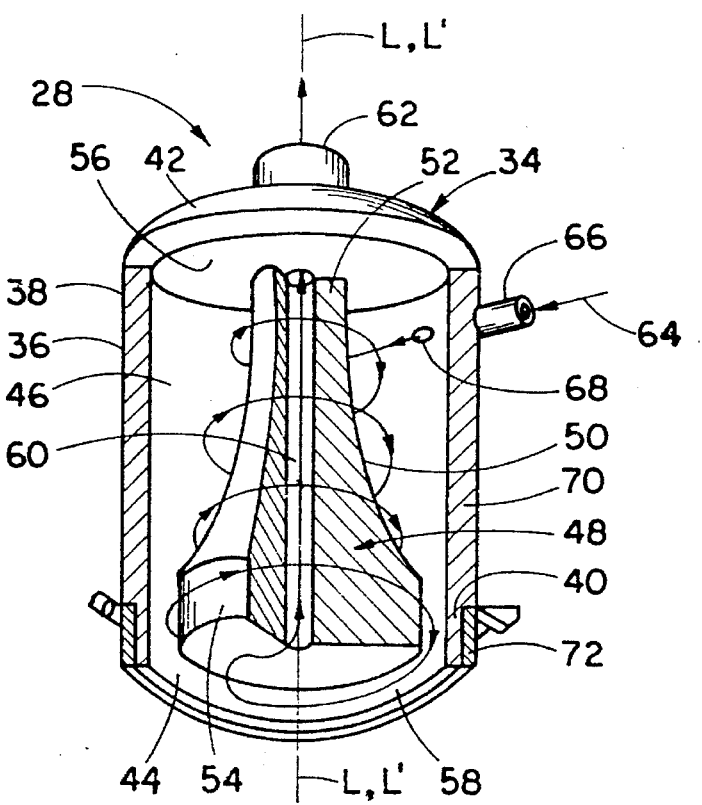
FIG. 2 is a perspective view, partially in section, of the flow-through sample cell of the present invention, illustrating a conical-shaped flow control body positioned within a housing and further illustrating how a liquid sample stream flows through the interior of the sample cell.

Now referring to FIG. 2, there is illustrated a perspective view, partially in section, of the flow-through sample cell 28 of the present invention. The flow-through sample cell 28 includes a housing 34 having a cylindrical body 36 with first and second end portions 38, 40. A first end wall 42 sealingly covers the cylindrical body at it's first end portion 38 and a second end wall 44 sealingly covers the cylindrical body 36 at it's second end portion 40. The cylindrical body 36, first end wall 42 and second end wall 44 are arranged to define a hollow interior 46 within the housing 34.

A conical-shaped flow control body 48 is positioned within the hollow interior 46 of the housing 34. The flow control body 48 has an outer surface 50 of ever-increasing diameter as the outer surface 50 extends between the first end portion 52 of the flow control body 48 and the second end portion 54 of the flow control body 48. The conical-shaped flow control body 48 is positioned within the hollow interior 46 of the housing 34 so that the first end portion 52 of the flow control body 48 abuts the interior surface 56 of the first end wall 42. The second end portion 54 of the flow control body is spaced from the second end wall 44 to define a gap or viewing area 58.

The conical-shaped flow control body 48 is also positioned within the hollow interior 46 of the housing 34 so that an axis L extending longitudinally through the flow control body 48 between it's first and second end portions 52, 54 is in registry with an axis L' extending longitudinally through the housing 34 between it's first and second end walls 42, 44. With the flow control body 48 positioned within the hollow interior 46 as described, a longitudinally extending flow channel 60 formed in the flow control body 48 is in registry with the pair of axes L, L' and is also aligned with a flow opening 62 formed in the first end wall 42 of the housing 34.

In order to utilize the flow-through sample cell 28 of the present invention, a liquid sample stream represented in FIG. 2 by the flow arrow 64 is passed through a hollow tube 66 communicating with an opening 68 defined in a wall 70 of the cylindrical body 36 and located at the first end portion 38 of the cylindrical body 36. The opening 68 defined in the wall 70 is oriented relative to the wall 70 so that the liquid sample stream 64 flowing through the tube 66 and through the opening 68 is introduced into the hollow interior 46 of the housing 34 along a flow path which is tangential to the outer surface 50 of the flow control body 48. Since the liquid sample stream 64 is introduced into the hollow interior 46 along a flow path tangential to the outer surface 50 of the flow control body 48, the liquid sample stream 64 is forced to flow by centrifugal action radially downwardly over the outer surface 50 of the flow control body 48 between the flow control body 48 first and second end portions 52, 54. As the liquid sample stream 64 flows in a spiral pattern by centrifugal action radially and downwardly over the outer surface 50 of the flow control body 48, the flow velocity of the sample stream 64 is increased due to a decrease in available volume within the hollow interior 46 of the housing 34 in the area of the second end portion 54 of the flow control body 48 due to the fact that the second end portion 54 is enlarged relative to the first end portion 52. The increase in flow velocity acts to displace liquid sample volume within the hollow interior 46 of the housing 34 and thus minimizes mixing of the incoming liquid sample stream 64 with the resident sample solution within the hollow interior 46 of the housing 34.

After the spirally-travelling liquid sample stream 64 leaves the area of the second end portion 54 of the flow control body 48, it flows radially across the viewing area 58 between the second end portion 54 of the flow control body 48 and the second end wall 44 of the housing 34. It is in this area of the housing 34 that a real-time analysis of the liquid sample stream 64 is conducted using analysis equipment such as the XRF analyzer 32 described with respect to FIG. 1. The second end wall 44 of the housing 34 is made from a clear sheet material which is chemically-inert and suitable for spectroscopic measurement and X-ray analysis, such as, a polypropylene, Teflon, mylar, beryllium or any similar such material. Thus, when the liquid sample stream 64 flows through the viewing area 58, an analyzer positioned adjacent to the clear second end wall 44 may view the liquid sample stream 64 and perform a non-contact, real-time analysis of the sample stream 64. As seen in FIG. 2, the second end portion 40 of the cylindrical body 36 is of a reduced diameter to receive a cylindrical retaining ring 72 operable to removably secure the clear second end wall 44 to the cylindrical body 36. After the liquid sample stream 64 is analyzed during it's flow through the viewing area 58, the liquid sample stream 64 flows upwardly through the flow channel 60 extending longitudinally through the center of the flow control body 48 and through the flow opening 62 formed in the first end wall 42 for return to the electrowinning cell 12 illustrated in FIG. 1.

As described, the flow-through sample cell 28, which may be made from any chemically-inert material that is suitable for spectroscopic analysis, such as polypropylene, Teflon, beryllium, or other suitable material resistant to corrosion, has a construction to centrifugally force a liquid sample stream to the viewing area 58 at the bottom of the sample cell where it is analyzed before exiting the sample cell 28. The tangential entrance of the liquid sample stream and the conical shape of the flow control body 48 are critical to obtaining a rapid response within the cell to changes in the sample stream. The decrease in available volume within the flow-through sample cell 28 in the direction of liquid sample stream flow and the tangential entrance of the liquid sample stream act to maintain radial flow of the sample stream within the cell. Maintaining the radial flow of liquid within the hollow interior 46 of the housing 34 essentially displaces resident sample volume with an incoming liquid sample volume rather than mixing of the resident and incoming sample volumes. This displacement of volume permits rapid and accurate responses to sample chemistry changes and also permits real-time analysis of the liquid sample stream when the sample stream enters the viewing area 58 of the cell 28.

It is thought that the present invention and many of its attendant advantages will be understood from the foregoing description and it will be apparent that various changes may be made in the form, construction and arrangement of the parts of the invention described herein without departing from the spirit and scope of the invention or sacrificing all of its material advantages, the form hereinbefore described being merely a preferred or exemplary embodiment thereof.

We claim:

1. A flow-through cell which operates in conjunction with a reflectance or fluorescence spectroscopy apparatus for analysis on a real-time basis of a sample from a low-volume, low-flow rate liquid stream, comprising:

(a) a cylindrical housing including an upper end wall having an outlet opening, a lower end wall made of a clear transparent material suitable for viewing a sample of a liquid stream passing over said lower end wall by a spectroscopy apparatus, and a curved sidewall defining a hollow interior and having an inlet opening displaced above said lower end wall; and (b) a cylindrical flow control body including an upper end, a lower end, and a conical shaped outer surface continuously increasing in diameter from said upper end to said lower end and having a longitudinally extending flow channel defined therethrough from said lower end to said upper end;

(c) said control body being positioned within said housing such that said upper end of said control body abuts said upper end wall of said housing to align said flow channel in communication with said outlet opening and such that said lower end of said control body is spaced a short axial distance above said lower transparent end wall of said housing to define a sample stream viewing area between said lower end of said control body and said lower end wall of said housing, said outer surface of said control body being displaced from an interior surface of said sidewall of said housing by a lateral distance continuously decreasing from said upper end to said lower end of said control body so as to continuously decrease available flow volume between said control body and said housing sidewall and thereby increase the flow velocity of a liquid stream that enters said inlet opening and flows radially about and centrifugally downwardly over said outer surface of said control body to said lower end thereof and then radially inwardly across said sample stream viewing area where real time analysis of a sample of said stream is taken by the spectroscopy apparatus before said stream exits up through said flow channel in said control body and out through said outlet opening of said upper end wall of said housing.

2. The flow-through cell as recited in claim 1, wherein said inlet opening is positioned at an upper end of said curved sidewall and so orientated such that said liquid stream entering said inlet opening is introduced along a flow path tangential to said outer surface of said flow control body.

3. The flow-through cell as recited in claim 1, wherein said clear transparent material of said lower end wall of said cylindrical housing is chemically-inert and is selected from the group consisting of polypropylene, Teflon, mylar and beryllium.

4. The flow-through cell as recited in claim 1, wherein said housing and said flow control body are made from a chemically-inert material suitable for spectroscopic analysis.

5. The flow-through cell as recited in claim 4, wherein said chemically-inert material is selected from the group consisting of polypropylene, Teflon, and beryllium.

\* \* \* \* \*